(12) United States Patent
Engman et al.

(10) Patent No.: US 6,626,911 B1
(45) Date of Patent: Sep. 30, 2003

(54) THREADED IMPLANT, AND ARRANGEMENT AND METHOD FOR SUCH AN IMPLANT

(75) Inventors: Fredrik Engman, Molnlycke (SE); Lars Jörnéus, Frillesas (SE)

(73) Assignee: Nobel Biocare AB, Gothenburg (SE)

( * ) Notice: Subject to any disclaimer, the term of this patent is extended or adjusted under 35 U.S.C. 154(b) by 0 days.

(21) Appl. No.: 09/831,020

(22) PCT Filed: Nov. 9, 1999

(86) PCT No.: PCT/SE99/02036

§ 371 (c)(1),
(2), (4) Date: Aug. 13, 2001

(87) PCT Pub. No.: WO00/27300

PCT Pub. Date: May 18, 2000

(30) Foreign Application Priority Data

Nov. 11, 1998 (SE) ................................................ 9803849

(51) Int. Cl.⁷ .............................................. A61B 17/56
(52) U.S. Cl. ........................ 606/73; 433/172; 433/173; 433/174
(58) Field of Search ............................ 606/73, 65, 70, 606/71, 72, 69; 433/169, 172, 173, 174, 175; 411/309, 307, 310, 311, 402, 403

(56) References Cited

U.S. PATENT DOCUMENTS

| 3,672,058 | A | | 6/1972 | Nikoghossian | ............... | 32/10 A |
|---|---|---|---|---|---|---|
| 4,960,381 | A | | 10/1990 | Niznick | ...................... | 433/174 |
| 5,207,132 | A | * | 5/1993 | Goss et al. | .................. | 411/402 |
| 5,580,246 | A | * | 12/1996 | Fried et al. | .................. | 433/172 |
| 5,810,590 | A | | 9/1998 | Fried et al. | .................. | 433/172 |
| 6,068,480 | A | * | 5/2000 | Misch et al. | ................. | 433/173 |

FOREIGN PATENT DOCUMENTS

| WO | WO 98/12982 | 4/1998 |
|---|---|---|
| WO | WO 98/31296 | 7/1998 |

* cited by examiner

Primary Examiner—Pedro Philogene
(74) Attorney, Agent, or Firm—Connolly Bove Lodge & Hutz LLP

(57) ABSTRACT

A threaded implant for screwing into jawbone and supporting a spacer element in the screwed-in position is provided. The implant includes a socket arrangement which can cooperate with a tool for screwing in the implant. The socket arrangement also secures the spacer element in an applied position. The socket arrangement includes two separate sockets, of which the first socket can cooperate with the tool and the second socket permits rotational locking of the spacer element.

29 Claims, 3 Drawing Sheets

THREADED IMPLANT, AND ARRANGEMENT AND METHOD FOR SUCH AN IMPLANT

TECHNICAL FIELD

The present invention relates to a threaded implant intended to be screwed into bone, preferably into jawbone. In the screwed-in position, the implant is intended to support at least one spacer element. The implant has a socket arrangement which can cooperate on the one hand with a tool, for screwing it in, and on the other hand with the respective spacer element for screwing the latter on securely when the implant is in position. The invention also relates to an arrangement for a threaded implant of the said type and to a method for anchoring the implant in bone, preferably jawbone.

PRIOR ART

Implants of the type in question can be provided with a part which projects upwards from the upper contact surface of the implant which is designed with a wrench grip which can be used when the implant is being screwed into the hole made, for example, in jawbone. The upwardly projecting part can also receive and fix in position (inter alia in the direction of rotation) the spacer element and, if appropriate, any attachments on the latter. When the implant is being screwed in, relatively high torsion forces (for example torsion forces of the order of 50–100 Newton centimetres) may be needed, which in itself requires special measures to be taken in respect of the implant arrangement. When the implant is being screwed in or inserted, so-called fixture holders are often used which constitute a form of intermediate element which is screwed securely into or onto the implant, which, by virtue of this, can obtain a temporary tool attachment. An existing wrench grip according to the above, which is relatively low, does not then need to be used at least at high insertion forces and in positions where it is difficult to access and use the whole height of the low wrench grip. The wrench grip does not need to be used as tool attachment, and because the fixture holder is screwed securely into or onto the implant, a stable locking is obtained between the fixture holder and the wrench grip. The use of a fixture holder or intermediate element also has the advantage that the implant in question can be supported, that is to say secured, by the tightening machine used for inserting the implant, and this, together with an often more reliable and simpler tightening function, means that the technique using the fixture holder has hitherto predominated.

General reference is made to the PCT specifications WO 98/12982 and 98/31296.

Reference is also made to U.S. Pat. No. 4,960,381 which relates to a completely different type of implant, namely a type which does not have the part projecting upwards from the contact surface for the spacer attachment according to the above, and where instead the tool and spacer element sockets have been combined in a common position inside the implant.

DESCRIPTION OF THE INVENTION
TECHNICAL PROBLEM

In order to achieve high torque transmission forces despite the small dimensions which exist in connection with implants, it is advantageous if the orientation of the drive surfaces on the tool socket and corresponding acting surfaces on the tool are arranged such that they extend as radially as possible. Thus, for example, with two cooperating polygons, see the case above with a wrench grip on an upwardly projecting part, there is always a wedging effect between the tool and the socket, which means that the stability is limited, especially in the tool socket if, as in this case, for reasons of biocompatibility, it is not possible to use hard materials in the implant, that is to say in the tool socket. The invention aims to solve these problems among others.

There are also disadvantages with using the above-mentioned fixture holders. Among other things, extra torque is needed for mounting and dismantling the respective fixture holder onto or from the respective implant. In addition, the torque which can be transmitted between fixture/implant and fixture holder is limited. Exceeding the admissible torque can lead to great difficulties when removing the fixture holder, which means that the fixture has to be reversed. Another defect which can arise is that the hexagon of the fixture is so greatly deformed that attachment of the spacer is made difficult or impossible, which means that the insertion and healing procedure has to be repeated. The invention also solves this set of problems by taking the technique in new directions.

It is also essential to be able to use conventional and well proven spacer elements. It is of great importance that such spacer elements can be used for reasons of compatibility and that they are well proven. The invention also solves this problem.

The tool socket must be able to withstand high torques in accordance with the above, and at the same time it is advantageous that the tool and the tool socket are designed so that a support function is made possible. The invention solves this problem too.

Using an internal fixture socket as spacer attachment (cf. the US patent specification mentioned above) can cause problems in obtaining sufficient stability of the spacer element. A spacer element in this context must have a projecting part which cooperates with the recess in the fixture. To lock the spacer in place with a screw connection, this projecting part must be made hollow so that a screw can pass through. This greatly reduces the stability. If the spacers are intended to cooperate with the internal tool socket, the spacers become very expensive and difficult to manufacture. It is also difficult or quite impossible to manufacture, at a reasonable cost, a socket of this kind when the aim is to ensure that the outer surface of the spacer element will form a smooth transition from the implant. The invention solves this problem too, with the realization that the spacer socket as such does not have any requirements, or only minimum requirements, in respect of torque transmission and instead it essentially constitutes a positioning instrument.

When internal fixture sockets are used as spacer attachments, there is also the problem of achieving sufficient stability of the spacer elements. The invention solves this problem too.

SOLUTION

The feature which can principally be regarded as characterizing a threaded implant in accordance with what has been stated above is that the socket arrangement comprises two geometrically separate sockets, of which the first socket can cooperate with the tool and the second socket permits rotational locking of the spacer element against the contact surface of the implant.

In further developments of the inventive concept, the second socket comprises a conventional socket of polygonal character, for example in the form of a hexagon socket. The latter can thus be assigned a spacer element in accordance with the previously used technique, and known and well proven spacer element structures can be used. The first socket can be arranged directly in the implant and thus not via the above-discussed fixture holders. The first socket can also be made internal and the second socket external. The second socket is arranged on a part projecting upwards from the contact surface of the implant, and the first socket is located essentially in the said projecting part, that is to say essentially above the contact surface of the implant. In an alternative embodiment, the first socket can be lowered inside the implant. The first socket can moreover comprise a number, preferably 4–6, of drive surfaces which can be acted on by the tool and which are arranged with salient or essentially radial extents. In further embodiments, the first socket can be arranged to accept a relatively high torque transmission force from the tool and at the same time have small dimensions in relation to the size of the implant and the internal socket. The first socket can also be arranged to permit a bearing function by means of the tool while it is being moved and used, for example a bearing function of the type which is described in the said WO 98/12982.

An arrangement according to the invention is characterized essentially in that the implant is provided with a first socket which can be assigned to the tool and a second socket geometrically separate from the first socket for receiving and rotationally locking the spacer element.

In further developments of the arrangement, it is proposed that a relatively high force applied by means of the tool on the first socket is prevented from mechanically affecting the second socket. The first socket can be arranged to meet a relatively high force application which can occur when the implant is screwed into the bone/jawbone despite small dimensions of the implant on account of the fact that the socket is internal. The second socket can be arranged to meet a relatively small force application which arises when the spacer element is applied, but can nevertheless operate with a precise positioning function.

A method according to the invention is characterized essentially in that the screwing-in is effected by means of a tool which is arranged on a tool socket provided in the implant and in that the spacer element is applied to a spacer element socket provided in the implant and separate from the tool socket.

Further developments of the method are characterized by the fact that a tool of star screwdriver type is arranged on an internal tool socket where, during screwing-in, the wing-shaped parts of the tool are pressed against essentially radially extending drive surfaces of the tool socket. The method also entails that conventional and well proven types of spacer elements can be applied to the spacer sockets of the implant in question.

ADVANTAGES

By means of what has been described above, it is no longer necessary to integrate the tool and spacer element sockets. These can each be made optimal and by means of the geometrical separation it is possible to ensure that application of force which has been effected in the tool socket does not mechanically affect or destroy the spacer element socket, which can therefore instead be used for precise positioning of the spacer element. An undamaged spacer element socket also contributes to a fully satisfactory implantation result. There is therefore no risk of the spacer socket being damaged and of the work of implantation and healing having to be repeated. The tool socket can be designed in a manner known per se, see specifications cited above, to permit simple bearing of the implant by means of the screwing tool (bore machine) used. The tool can be manufactured to meet high precision demands, which is economically defensible since the tool can be used for a very large number of implant fittings.

DESCRIPTION OF THE FIGURES

A presently proposed embodiment of a threaded implant, an arrangement and a method according to the invention will be described below with reference to the attached drawings, in which.

DETAILED EMBODIMENT

Figure 1:
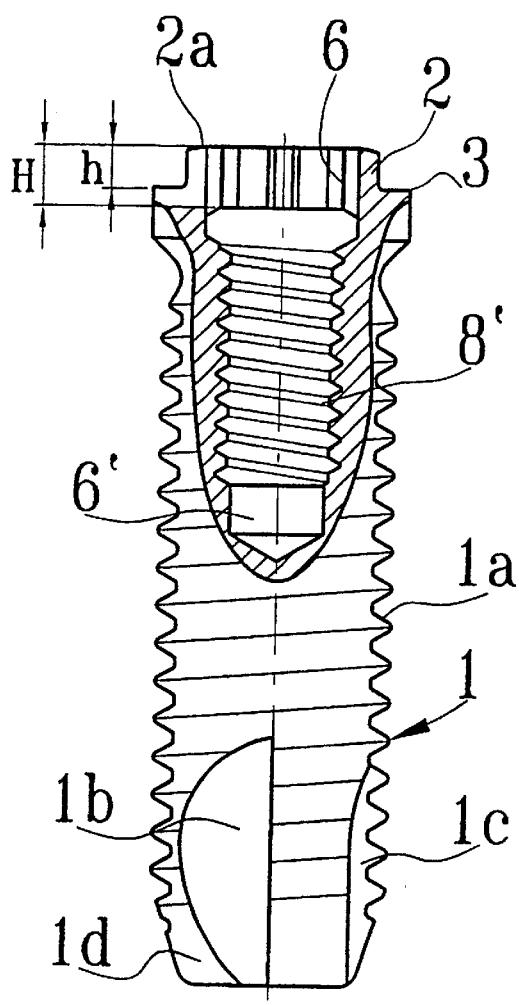
FIG. 1 shows, in a side view and partial longitudinal section, an example of a threaded implant which has the tool and spacer element sockets geometrically separated.
Figure 2:
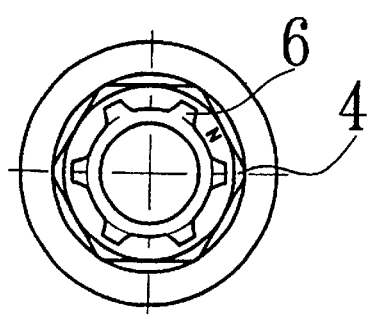
FIG. 2 shows a top view of the implant according to FIG. 1.
Figure 3:
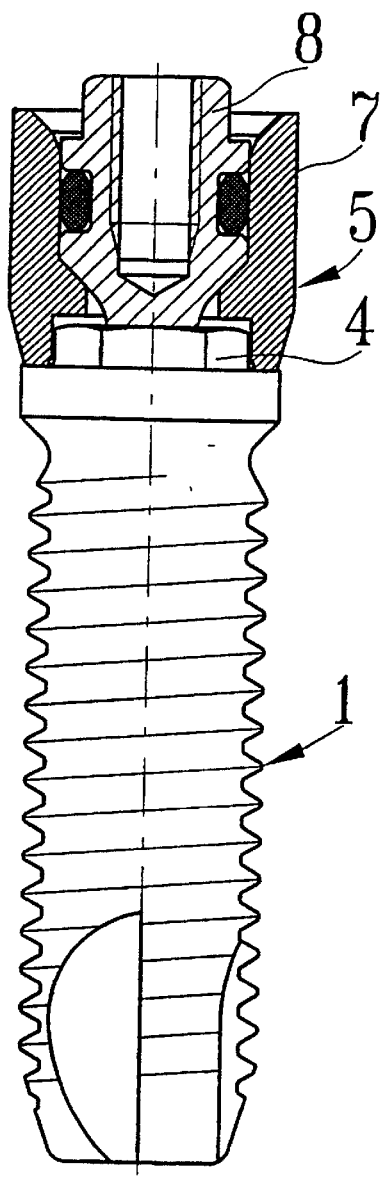
FIG. 3 shows a side view of the implant according to FIG. 1, where a spacer element is arranged on the spacer element socket.

FIGS. 1 and 2 show an example of a type of implant 1 which the present invention is intended to be used on. The implant has, inter alia, a part 2 which projects upwards above the top surface or contact surface 3 of the implant. The upwardly projecting part 2 is provided with a wrench grip 4, for example a wrench grip in the form of a polygon which in the present case can be a hexagon. Arranged on the top surface and polygon there is a spacer element 5 which can be of a type known per se, FIG. 3, and will therefore not be described in detail here. Arranged inside the upwardly projecting part and the implant there are internal axial groves 6 which can alternatively have a position 6' lower down in the implant. The grooves have a height H and extend from the top surface 2a of the upwardly projecting part 2. The height of the upwardly projecting part above the contact surface 3 is indicated by h. The height H exceeds the height h and the grooves thus come to extend both in the upwardly projecting part and in the implant body situated below the latter. The implant also has an external thread 1a and bone chip hollows 1b, 1c. In addition, there is a front conical part 1d, and the thus threaded implant, which is designed to be self-tapping, is intended to be screwed into a hole prepared in the jawbone. The type of implant is well known as such and will therefore not be described in detail here.

The axial inner grooves 6 are arranged to be used as a tool socket for a tool which is described below. The polygon 4 is intended to be used as a spacer element socket for the element 5, which in a known manner comprises a spacer sleeve 7 and a locking screw 8 which cooperates with an inner bore 8' in the upper part of the implant. The active part of the tool socket is situated essentially in or near the upwardly projecting part 2 and can therefore be regarded as corresponding to the said height h.

Figure 4:
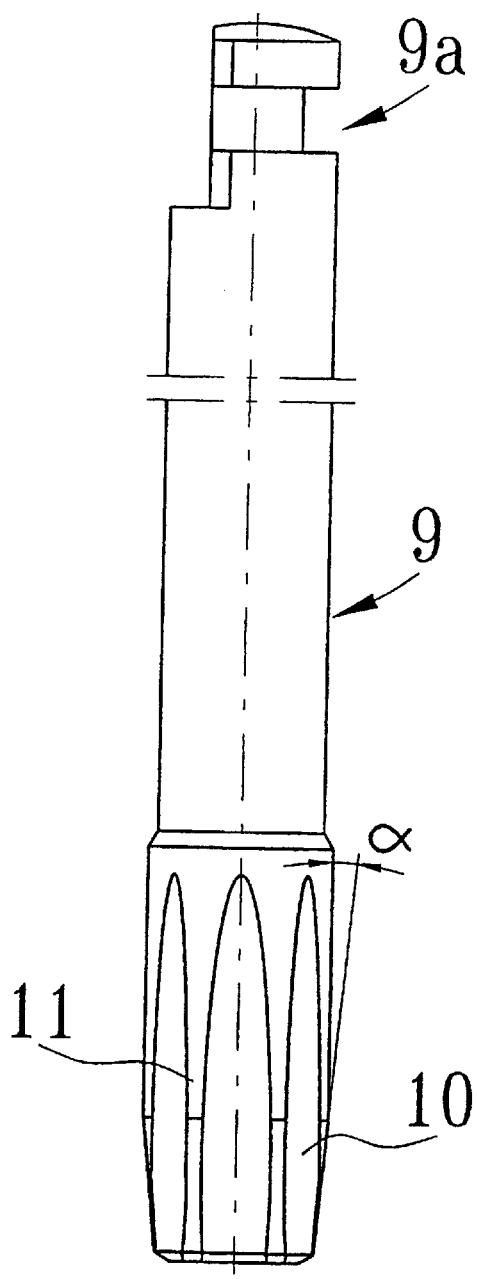
FIG. 4 shows a side view of the tool by means of which an implant according to FIGS. 1–3 can be screwed into a hole in the jawbone.

FIG. 4 shows a tool part 9 which can be coupled to an electrically operated or otherwise operated (pneumatically, hydraulically, etc.) motor (not shown) via its upper part 9a which has an attachment for the drive motor. At its other end, the tool is provided with cup-like recesses 10 for forming wing-shaped elements 11. A cone angle α is chosen at about 5°, for example 5.5°. The recesses in this case have a length of about 5 mm and the diameter is about 2.5 mm.

Figure 5:
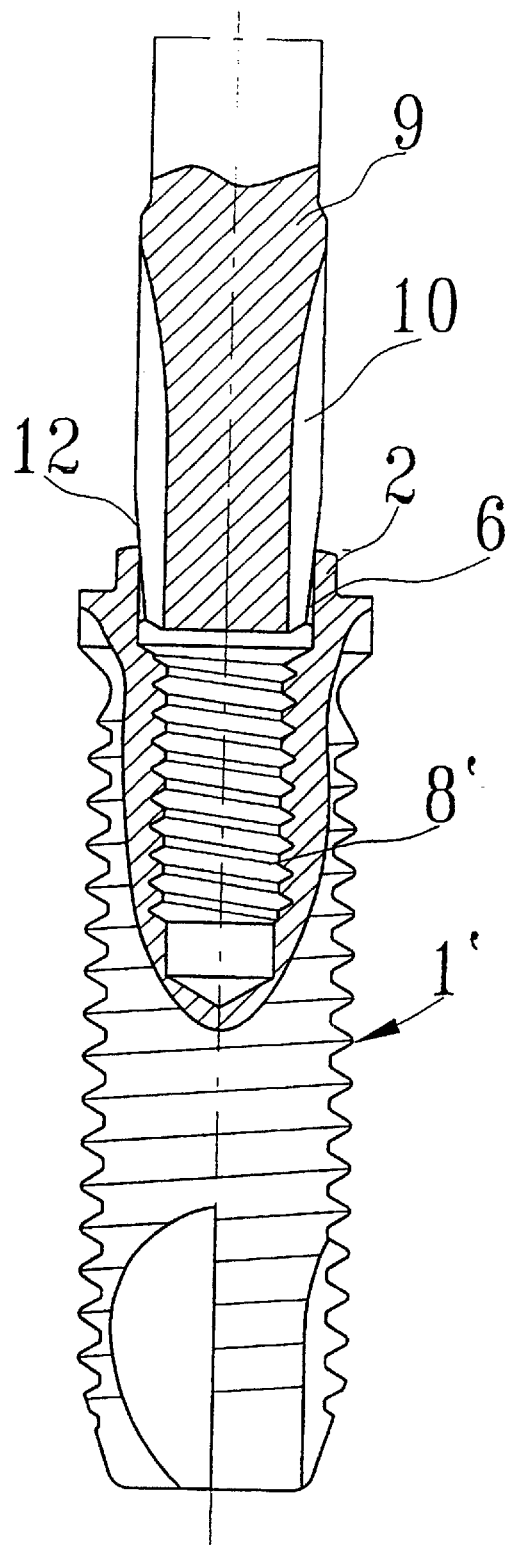
FIG. 5 shows a side view and partial cutaway view of the front parts of the tool 3 where the tool exerts a support function on an implant according to FIG. 1.

FIG. 5 shows the cooperation between the tool 9 and the tool socket of the implant. By means of a cone shape 12 on the front part of the tool, a bearing function for the implant 1' is obtained via the axial grooves 6.

Figure 6:
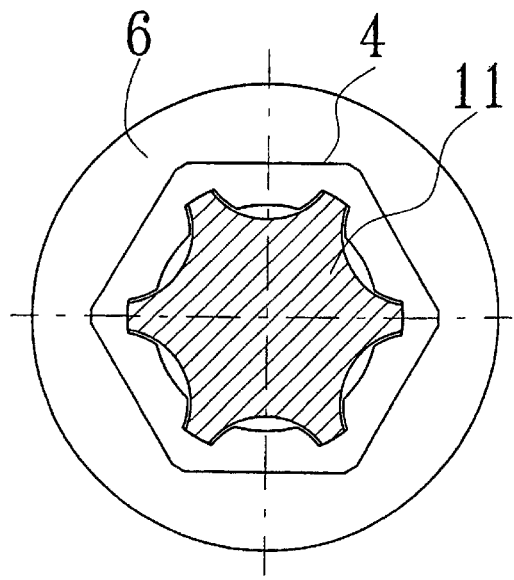
FIG. 6 shows a top view of the application of the tool according to FIG. 4 in the tool socket in the implant, where the tool and the implant assume a starting position.

In FIG. 5, the recesses of the tool are indicated by 10 and the wing-shaped elements by 11. The recesses have curved bottom parts. The number of recesses and wings in this embodiment is six. The axial grooves 6 in the upwardly projecting part 2 of the implant 1 have shapes which correspond to the outer shapes of the wings. FIG. 6 shows the case where the tool has been applied with the wings 11 in the grooves 6, but where it has not yet begun to be turned.

Figure 7:
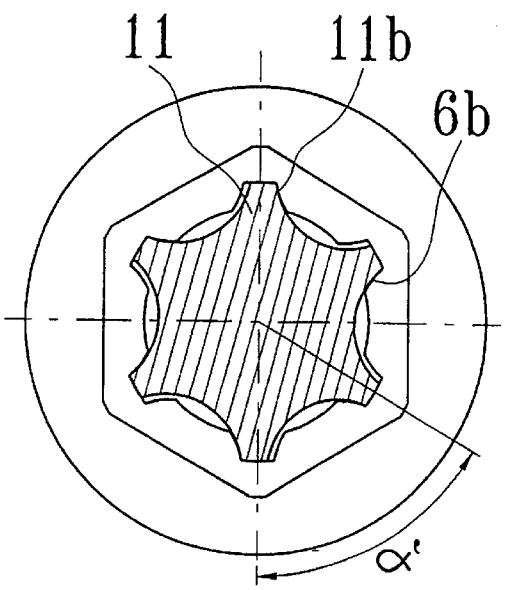
FIG. 7 shows a top view of the stage in which the tool has been turned in relation to the implant compared to FIG. 6.
Figure 8:
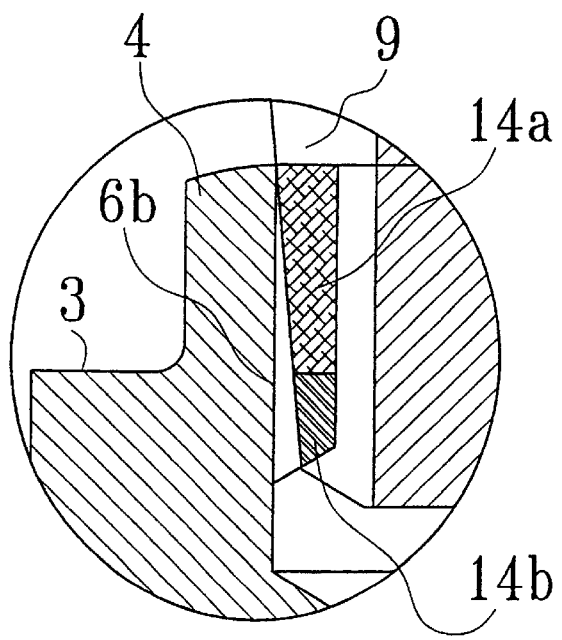
FIG. 8 shows an enlarged view of the cooperation between the front part of the tool and the groove side walls of the tool socket.
Figure 9:
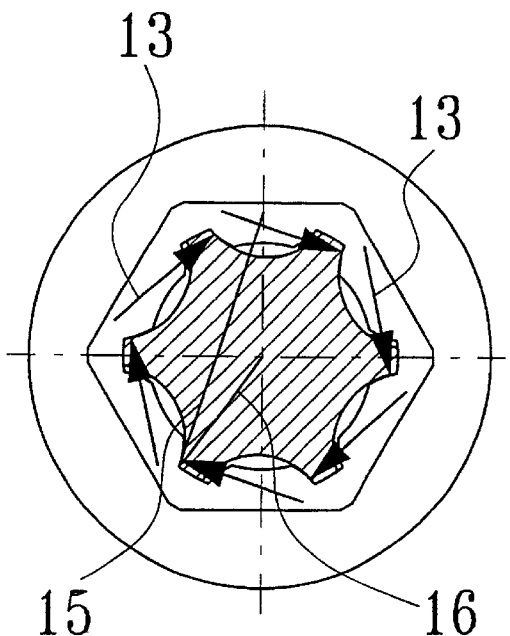
FIG. 9 shows a view corresponding to FIG. 8, but with the drive force directions indicated.

FIG. 7, the tool has begun to be turned so that the side surfaces 11b of the wings 11 function as drive surfaces against the groove side walls 6b in the upwardly projecting part 2 (see FIG. 5). The grooves are situated in relation to each other at an angle of α' which in the present case is 60°. The side walls 11b act on the groove walls 6b as a result of the turning movement essentially in a tangential direction, which is shown by the arrows 13 in FIG. 9. The side surfaces of the wing-shaped elements are, like the groove surfaces, also curved and, during the driving or the drive function, the curved surfaces bear against each other across extensive parts or areas 14a and 14b, which are shown in FIG. 8. The length of the said extensive parts corresponds essentially to the groove depth of the said grooves. It will be seen from the figure that the greater part of the said surfaces is located above the upper contact surface of the implant body. FIG. 9 also indicates the direction of extension 15 of the contact surface compared to the actual radial direction 16 of the drive plane.

The invention is not limited to the embodiment given above by way of example, but can be modified within the scope of the attached patent claims and the inventive concept.

What is claimed is:

1. Threaded implant for being screwed into bone and, in the screwed-in position, to support at least one spacer element comprising a socket arrangement which can cooperate with a tool for screwing in the socket arrangement and with the at least one spacer element for securing the at least one spacer element in the applied position against a contact surface of the implant, the socket arrangement comprising two geometrically separate sockets, said two sockets comprising a first socket for cooperating with the tool and a second socket for permitting rotational locking of the at least one spacer element against the contact surface, wherein the first socket is disposed internal of the second socket.

2. Implant according to claim 1, wherein the second socket comprises a conventional socket of polygonal character and is assigned the spacer element.

3. Implant according to claim 1, wherein the first socket is internal and the second socket is external.

4. Implant according to claim 1, wherein the second socket is arranged on a part projecting upwards from the contact surface of the implant.

5. Implant according to claim 4, wherein the first socket is located essentially adjoining the upwardly projecting part.

6. Implant according to claim 1, wherein the first socket is located inside the implant.

7. Implant according to claim 6, wherein the first socket extends from the top surface of the upwardly projecting part.

8. Implant according to claim 1, wherein the first socket comprises a number of drive surfaces which can be acted on by the tool and which are arranged with salient or essentially radial extents.

9. Implant according to claim 1, wherein the first socket is arranged to permit a bearing function by means of the tool.

10. Implant according to claim 2, wherein the first socket is internal and the second socket is external.

11. Implant according to claim 2, wherein the second socket is arranged on a part projecting upwards from the contact surface of the implant.

12. Implant according to claim 3, wherein the second socket is arranged on a part projecting upwards from the contact surface of the implant.

13. Implant according to claim 1, wherein the bone is a jawbone.

14. Implant according to claim 1, wherein the first socket is arranged inside the upwardly projecting second socket.

15. Implant according to claim 1, wherein the first socket arranged in a position lower than the second socket.

16. Implant according to claim 2, wherein the polygonal character shape is in the form of a hexagon.

17. Implant according to claim 8, wherein the number of drive surfaces is about 4–6.

18. Arrangement for a threaded implant for permitting application of screwing force by means of a screwing-in tool and for positioning and securing, in the screwed-in position of the implant, at least one spacer element against a contact surface of the implant, the implant comprising a first socket which can be assigned to the tool, and a second socket geometrically separate from the first socket and used for receiving and securing the spacer element against the said contact surface, the first socket internal of the second socket.

19. Arrangement according to claim 18, wherein a force applied by means of the tool on the first socket is prevented from mechanically affecting the second socket.

20. Arrangement according to claim 18, wherein the first socket is arranged to meet a relatively high force application which can occur when the implant is screwed into the bone despite small dimensions of the implant on account of the fact that the socket is internal.

21. Arrangement according to claim 18, wherein the second socket is arranged to meet a relatively small force application which arises when the spacer element is applied.

22. Implant according to claim 18, wherein the first socket is arranged inside the upwardly projecting second socket.

23. Implant according to claim 18, wherein the first socket is arranged lower than the second socket.

24. Method for anchoring a threaded implant in a jawbone and applying at least one spacer element to contact a surface of the implant in the screwed-in position of the implant, comprising screwing-in the implant by means of a tool which is arranged on a tool socket provided in the implant and applying the spacer element to a spacer element socket provided in the implant and separate from the tool socket, wherein the tool socket is disposed internal of the spacer element socket.

25. Method according to claim 24, wherein the tool is arranged against an internal tool socket and is designed to ensure a bearing function for the implant.

26. Method according to claim 24, wherein a tool of star screwdriver type is arranged against an internal tool socket where, during screwing-in, the wing-shaped parts of the tool are pressed against essentially radially extending surfaces in the tool socket.

27. Method according to claim 25, wherein conventional and well proven types of spacer elements can be applied to the spacer element socket.

28. Method according to claim 24, wherein the spacer element socket is upwardly projecting.

29. Method according to claim 24, wherein the tool socket is arranged lower than the spacer element socket.

* * * * *